(12) United States Patent
Eldred et al.

(10) Patent No.: US 6,544,960 B1
(45) Date of Patent: Apr. 8, 2003

(54) CHEMICAL COMPOUNDS

(75) Inventors: Colin David Eldred, Stevenage (GB); Andrew Michael Kenneth Pennell, San Francisco, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/530,575

(22) PCT Filed: Nov. 6, 1998

(86) PCT No.: PCT/EP98/07023

§ 371 (c)(1), (2), (4) Date: Jun. 15, 2000

(87) PCT Pub. No.: WO99/24451

PCT Pub. Date: May 20, 1999

(30) Foreign Application Priority Data

Nov. 8, 1997 (GB) .............................. 9723590

(51) Int. Cl.⁷ .................... A61K 31/70; C07H 19/167
(52) U.S. Cl. .................. 514/46; 536/27.62; 536/27.63
(58) Field of Search .................. 514/46; 536/27.62, 536/27.63

(56) References Cited

U.S. PATENT DOCUMENTS

| | | | | |
|---|---|---|---|---|
| 4,738,954 A | * | 4/1988 | Hamilton et al. | 514/46 |
| 4,843,066 A | * | 6/1989 | Yamada et al. | 514/45 |
| 4,868,160 A | * | 9/1989 | Hamilton et al. | 514/46 |
| 5,364,862 A | * | 11/1994 | Spada et al. | 514/303 |
| 5,561,134 A | * | 10/1996 | Spada et al. | 514/266 |
| 5,589,467 A | * | 12/1996 | Lau et al. | 514/46 |
| 5,652,366 A | * | 7/1997 | Spada et al. | 546/118 |
| 5,705,491 A | * | 1/1998 | Yamada et al. | 514/46 |
| 5,736,554 A | * | 4/1998 | Spada et al. | 514/303 |
| 5,773,603 A | * | 6/1998 | Yamada et al. | 514/46 |
| 5,998,388 A | * | 12/1999 | Ellis et al. | 514/46 |

FOREIGN PATENT DOCUMENTS

| | | | |
|---|---|---|---|
| JP | 07 118156 A2 | * | 5/1995 |
| WO | W O 92/05177 A1 | * | 4/1992 |
| WO | WO 95 07921 A | | 3/1995 |
| WO | 9528160 | * | 10/1995 |
| WO | W O 95/28160 A1 | * | 10/1995 |
| WO | W O 97/33590 A1 | * | 9/1997 |
| WO | WO 97 33591 A | | 9/1997 |
| WO | W O 97/33591 A1 | * | 9/1997 |
| WO | WO 97 43300 A | | 11/1997 |
| WO | WO 98 01426 A | | 1/1998 |

OTHER PUBLICATIONS

Poulsen et al., "Adenosine Receptors: New Opportunities for Future Drugs," *Bioorganic & Medicinal Chemistry*, 6, 619–641 (1998).*

Lubitz Von D.K.J.E. et al., "Reduction of Postichemic Brain Damage and Memory Dificits Following Treatment with the Selective Adenosine A1 Receptor Agonist" European Journal of Pharmacology, P002035719 302, 43–48 (1996).

* cited by examiner

*Primary Examiner*—Johann Richter
*Assistant Examiner*—L. E. Crane
(74) *Attorney, Agent, or Firm*—Bacon & Thomas

(57) ABSTRACT

A compound of formula (I), wherein $R^2$ represents $C_{1-3}$alkyl, halogen or hydrogen; $R^3$ represents straight or branched alkyl group of 1–6 carbon atoms; with the proviso that, when $R^3$ represents $C_{1-3}$alkyl, $R^2$ represents $C_{1-3}$alkyl, $R^1$ cannot represent phenyl optionally substituted by one or more substituents selected from halogen, $C_{1-3}$alkyl, trifluoromethyl, nitro, cyano, $-CO_2R^c$, $-CONR^cR^d$, $-COR^c$, $-SOR^e$, $SO_2R^e$, $-SO_3H$, $-SO_2NR^cR^d$, $-OR^c$, $-NHSO_2R^e$, $-NHCOR^c$ and $-NR^cR^d$; and salts and solvates thereof, in particular, physiologically acceptable solvates and salts thereof. These compounds are agonists at the Adenosine A1 receptor.

17 Claims, No Drawings

CHEMICAL COMPOUNDS

The present invention relates to novel adenosine derivatives, to processes for their preparation, to pharmaceutical compositions containing them and to their use in medicine.

Thus the invention provides compounds of formula (I) which are agonists at the adenosine A1 receptor.

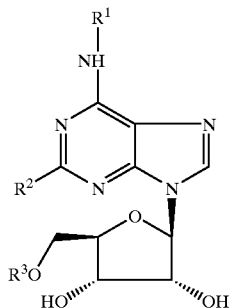

(I)

wherein $R^2$ represents $C_{1-3}$alkyl, halogen or hydrogen;

$R^3$ represents straight or branched alkyl group of 1–6 carbon atoms;

$R^1$ represents a group selected from (1) -(alk)$_n$-(C$_{3-7}$) cycloalkyl, including bridged cycloalkyl, said cycloalkyl group being optionally substituted by one or more substituents selected from OH, halogen, —(C$_{1-3}$) alkoxy, wherein (alk) represents $C_{1-3}$alkylene and n represents 0 or 1.

(2) an aliphatic heterocyclic group of 4 to 6 membered rings containing at least one heteroatom selected from O, N or S, optionally substituted by one or more substituents selected from the group consisting of —(C$_{1-3}$)alkyl, —CO$_2$—(C$_{1-4}$) alkyl, —CO(C$_{1-3}$ alkyl), —S(=O)$_n$—(C$_{1-3}$alkyl), CONR$^a$R$^b$ (wherein R$^a$ and R$^b$ independently represent H or C$_{1-3}$alkyl) or =O, and where there is a sulfur atom in the heterocyclic ring, said sulfur is optionally substituted by (=O)$_n$ where n is 1 or 2.

(3) Straight or branched $C_{1-12}$ alkyl, optionally including one or more O, S(=O)$_n$, (where n is 0, 1 or 2) or N groups substituted within the alkyl chain, said alkyl optionally substituted by one or more of the following groups, phenyl, halogen, hydroxy or NR$^a$R$^b$ wherein R$^a$ and R$^b$ both represent C$_{1-3}$alkyl or hydrogen.

(4) a fused bicyclic aromatic ring

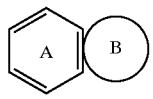

wherein B represents a 5 or 6 membered heterocyclic aromatic group containing 1 or more O, N or S atoms, wherein the bicyclic ring is attached to the nitrogen atom of formula (I) via a ring atom of ring A and ring B is optionally substituted by —CO$_2$ (C$_{1-3}$alkyl).

(5) a phenyl group optionally substituted by one or more substituents selected from:
-halogen, —SO$_3$H, -(alk)$_n$OH, -(alk)$_n$-cyano, —(O)$_n$—C$_{1-6}$-alkyl (optionally substituted by one or more halogens), -(alk)$_n$-nitro, —(O)$_m$-(alk)$_n$—CO$_2$R$^c$, -(alk$_n$) —CONR$^c$R$^d$, -(alk)$_n$—COR$^c$, -(alk)$_n$—SOR$^e$, -(alk)$_n$—SO$_2$R$^e$, -(alk)$_n$ SO$_2$NR$^c$R$^d$, -(alk)$_n$OR$^c$, -(alk)$_n$(CO)$_m$NHSO$_2$R$^e$, -(alk)$_n$—NHCOR$^c$, -(alk)$_n$—NR$^c$R$^d$ wherein m and n are 0 or 1 and alk represents a $C_{1-6}$alkylene group or $C_{2-6}$ alkenyl group.

(6) A phenyl group substituted by a 5 or 6 membered heterocyclic aromatic group, said heterocyclic aromatic group optionally being substituted by $C_{1-3}$alkyl or NR$^c$R$^d$.

$R^c$ and $R^d$ may each independently represent hydrogen, or $C_{1-3}$ alkyl or when part of a group NR$^c$R$^d$, R$^c$ and R$^d$ together with the nitrogen atom may form a 5 or 6 membered heterocyclic ring optionally containing other heteroatoms which heterocyclic ring may optionally be substituted further by one or more $C_{1-3}$ alkyl groups.

$R^e$ represents $C_{1-3}$alkyl;

With the proviso that, when $R^3$ represents $C_{1-6}$ alkyl, $R^2$ represents $C_{1-3}$ alkyl, $R^1$ cannot represent phenyl optionally substituted by one or more substituents selected from halogen, $C_{1-3}$alkyl, trifluoromethyl, nitro, cyano, —CO$_2$R$^c$, —CONR$^c$R$^d$, —COR$^c$, —SOR$^e$, —SO$_2$R$^e$, —SO$_3$H, —SO$_2$NR$^c$R$^d$, —OR$^c$, —NHSO$_2$R$^e$, —NHCOR$^c$ and —NR$^c$R$^d$;

and salts and solvates thereof, in particular, physiologically acceptable solvates and salts thereof.

Conveniently, the adenosine A1 agonists of general formula (I) above exhibit greater activity at the adenosine receptor than the other adenosine receptor subtypes, particularly A3. More preferably the compounds exhibit little or no activity at the adenosine A3 receptor.

It will be appreciated that wherein $R^1$ and/or $R^2$ in compounds of formula (I) contain one or more asymmetric carbon atoms the invention includes all diastereoisomers of compounds of formula (I) and mixtures thereof. Otherwise the stereochemical configuration of compounds of the invention is as depicted in formula (I) above.

As used herein, the term "alkyl" means a straight or branched chain alkyl group. Examples of suitable alkyl groups within $R^1$ and $R^2$ include methyl, ethyl, n-propyl, i-propyl, n-butyl, s-butyl, t-butyl and 2,2-dimethylpropyl.

As used herein, the term "$C_{2-6}$alkenyl" means a straight or branched chain alkenyl group containing 2 to 6 carbon atoms. Allyl represents an example of a suitable $C_{2-6}$alkenyl group.

As used herein the term "alkylene" means a straight or branched chain alkylene group containing 1 to 6 carbon atoms e.g. methylene.

The term "halogen" means fluorine, chlorine, bromine or iodine.

By aliphatic heterocyclic group is meant a cyclic group of 4–6 carbon atoms wherein one or more of the carbon atoms is/are replaced by heteroatoms independently selected from nitrogen, oxygen or sulfur. This group may optionally be substituted as defined hereinabove.

The term heterocyclic aromatic group refers to an aromatic mono or bicyclic ring system comprising from 5 to 10 carbon atoms wherein one or more of the carbon atoms is/are replaced by heteroatoms independently selected from nitrogen, oxygen and sulfur, which ring system may optionally be substituted as defined hereinabove.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. A particularly suitable pharmaceutically acceptable salt of the compounds of formula (I) is the hydrochloride salt. Other acids such as oxalic, while not, in themselves pharmaceutically acceptable, may be useful as intermediates in obtaining the compounds of the invention and their pharmaceutically acceptable acid addition salts. The solvates may be, for example, hydrates.

$R^3$ preferably represents a $C_{1-3}$ alkyl group especially a methyl or ethyl group more preferably methyl.

$R^2$ preferably represents hydrogen, methyl or halogen, more preferably hydrogen or methyl.

Conveniently, $R^1$ may represent $(alk)_n$- $C_{5-7}$ cycloalkyl, including bridged cycloalkyl wherein n is 0 or 1 and the said cycloalkyl is either substituted by at least one substituent selected from halogen, particularly fluorine, —($C_{1-3}$) alkoxy, particularly methoxy and OH or is unsubstituted. Preferably, when substituted the substituent is fluorine and, the cycloalkyl is mono-substituted. Preferably, n represents zero.

Alternatively $R^1$ may represent a substituted or unsubstituted aliphatic heterocyclic group, which when substituted, the substituent being selected from the group consisting Of $C_{1-3}$alkyl, —($CO_2$)—($C_{1-4}$)alkyl, =O, —CO—($C_{1-3}$)alkyl, —S(=O)$_n$—($C_{1-3}$)alkyl (where n is 1 or 2), CONR$^a$R$^b$ wherein R$^a$ and R$^b$ are defined herein above, and when there is a heteroatom S in the ring, this S is optionally substituted by (=O)$_n$ where n is 1 or 2. More preferably the substituents are —$CO_2C_{(1-4)}$alkyl or methyl.

Conveniently the aliphatic heterocyclic group is unsubstituted or when the substituent is —$CO_2(C_{1-4})$alkyl the heteroatom is N and the substituent is directly attached to said ring nitrogen atom.

Preferably the heterocyclic ring is 6 membered and more preferably contains only one N, O or S heteroatom.

Alternatively, $R^1$ may represent a straight or branched alkyl of 1–6 carbon atoms optionally including at least one S (=O)$_2$, O or N substituted in the chain. The alkyl group conveniently may be further substituted by at least one group selected from OH, phenyl and fluorine or is unsubstututed.

Alternatively $R^1$ may represent a phenyl group which is substituted by one or more substituents selected from OH, halogen, (O)$_m$ (alk)$_n$ $CO_2R^c$, and -(alk)$_n$OH. Preferably the phenyl is disubstituted in the 2,4 positions. Preferably both substituents are halogen more particularly, fluorine and chlorine. For example, a particularly preferred combination is 2- fluoro and 4- chloro.

Alternatively $R^1$ represents a phenyl group substituted by a 5-tetrazolyl group, this group itself optionally substituted by $C_{1-3}$alkyl.

Alternatively $R^1$ represents a fused group.

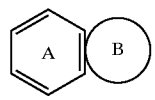

wherein B represents a furan ring, said furan ring being optionally substituted by —$CO_2(C_{1-3})$alkyl more preferably in the 2 position.

It is to be understood that the present invention covers all combinations of particular and preferred groups mentioned above.

Particular compounds according to the invention include:

5'-O-Methyl-N-(tetrahydro-furan-3R-yl)-adenosine

N-(2R-Hydroxy-(R)-cyclopentyl)-5'-O-methyl-adenosine

5'-O-Methyl-N-(tetrahydro-pyran4-yl)-adenosine

N-(2S-Methoxy-(S)-cyclopentyl)-5'-O-methyl-adenosine

5'-O-Methyl-N-(2S-methyl-tetrahydro-furan-3R-yl)-adenosine

N-(3-Chloro4-hydroxy-phenyl)-5'-O-methyl-adenosine

5'-O-Methyl-N-(1R-methyl-2-phenyl-ethyl)-adenosine

N-tert-Butyl-5'-O-methyl-adenosine

N-(2S-Fluoro-(S)-cyclopentyl)-5'-O-methyl-adenosine

N-(2, 3-Dihydroxy-propylamino)-5'-O-methyl-adenosine

N-rel-[(1S,4R)-Bicyclo[2.2.1]hept-2R-yl]-5'-O-methyl-adenosine

4-[9-(3R,4S-Dihydroxy-5R-methoxymethyl-tetrahydro-furan-2R-yl)-9H-purin-6-ylamino]-piperidine-1-carboxylic acid ethyl ester 5'-O-Methyl-N-[4-(2-methyl-2H-tetrazol-5-yl)-phenyl]-adenosine 3-{4-[9-(3R,4S-Dihydroxy-5R-methoxymethyl-tetrahydro-furan-2R-yl)-9H-purin-6-ylamino]-phenyl}-(E)-acrylic acid N-(4-Hydroxymethyl-phenyl)-5'-O-methyl-adenosine {4-[9-(3R,4S-Dihydroxy-5R-methoxymethyl-tetrahydro-furan-2R-yl)-9H-purin-6-ylaminol]-phenoxy}acetic acid 5-[9-(3R,4S-Dihydroxy-5R-methoxymethyl-tetrahydro-furan-2R-yl)-9H-purin-6-ylaminol]-benzofuran-2-carboxylic acid methyl ester 5'-O-Methyl-N-(tetrahydro-thiopyran4-yl)-adenosine N-rel-[(1R,5R)-Bicyclo[3.2.0]hept-6S-yl]-5'-O-methyl-adenosine 4-[9-(3R,4S-Dihydroxy-5R-methoxymethyl-tetrahydro-furan-2R-yl)-2-methyl-9H-purin-6-ylamino]-piperidin-2-one 5'-O-Methyl-N-(1S-methoxymethyl-2-methyl-propyl)-adenosine N-(2-Hydroxy-1R-methyl-ethyl)-5'-O-methyl-adenosine N-(2-Fluoro-1R-methyl-ethyl)-5'-O-methyl-adenosine N-(1S-Fluoromethyl-2-methoxy-ethyl)-5'-O-methyl-adenosine N-(3-Amino-propyl)-5'-O-methyl-adenosine 2-[9-(3R,4S-Dihydroxy-5R-methoxymethyl-tetrahydro-furan-2R-yl)-2-methyl-9H-purin-6-ylamino]-acid methylamide N-Cyclopentyl-2-methyl-5'-O-methyl-adenosine N-Cyclopropylmethyl-2-methyl-5'-O-methyl-adenosine Compounds according to the invention have applicability as inhibitors of lipolysis i.e. they decrease plasma free fatty acid concentrations. The compounds may thus be used in the treatment of hyperlipidaemias. Furthermore, as a consequence of their anti-lipolytic activity, the compounds have the ability to lower elevated blood glucose, insulin and ketone body levels and therefore may be of value in the therapy of diabetes. Since anti-lipolytic agents have hypolipidaemic and hypofibrinogenaemic activity, the compounds may also show anti-atherosclerotic activity. The anti-lipolytic activity of compounds of the invention has been demonstrated by their ability to lower the concentration of non-esterified fatty acids (NEFA) in starved rats dosed orally according to the method described by P. Strong et al. in Clinical Science (1993), 84, 663–669.

In addition to their anti-lipolytic effect, the compounds of the invention may independently affect cardiac function by reducing heart rate and conduction. The compounds may thus be used in the therapy of a number of cardiovascular disorders, for example cardiac arrythmias, particularly following myocardial infarction, and angina.

Furthermore, the compounds of the invention are useful as cardioprotective agents, having applicability in the treatment of ischaemic heart disease. As used herein the term "ischaemic heart disease" includes damage associated with both myocardial ischaemia and reperfusion, for example, associated with coronary artery bypass grafting (CABG), percutaneous translumenal coronary angioplasty (PTCA), cardioplegia, acute myocardial infarction, thrombolysis, stable and unstable angina and cardiac surgery including in particular cardiac transplantation. The compounds of the invention additionally are useful for treating ischaemic damage to other organs. The compounds of the invention may also be valuable in the treatment of other disorders arising as a result of widespread atheromatous disease, for example, peripheral vascular disease (PVD) and stroke.

The compounds may also inhibit renin release and thus be of use in the therapy of hypertension and heart failure. The compounds may also be useful as CNS agents (e.g. as hypnotics, sedatives, analgesics and/or anti-convulsants particularly finding use in the treatment of epilepsy).

In addition, the compounds of the invention may find use in the treatment of sleep apnoea.

The compound of formula (I) and pharmaceutically acceptable acid addition salts thereof are useful as analgesics. They are therefore useful in treating or preventing pain. They may be used to improve the condition of a host, typically of a human being, suffering from pain. They may be employed to alleviate pain in a host. Thus, the compound of formula (I) and its pharmaceutically acceptable acid addition salts may be used as a preemptive analgesic to treat acute pain such as musculoskeletal pain, post operative pain and surgical pain, chronic pain such as chronic inflammatory pain (e.g. rheumatoid arthritis and osteoarthritis), neuropathic pain (e.g. post herpetic neuralgia, neuropathies associated with diabetes, trigeminal neuralgia and sympathetically maintained pain) and pain associated with cancer and fibromyalgia. The compound of formula (I) may also be used in the treatment or prevention of pain associated with migraine, tension headache and cluster headaches, pain associated with functional bowel disorders (eg IBS), non cardiac chest pain and non ulcer dyspepsia.

Accordingly, the invention provides a compound of formula (I) or a physiologically acceptable salt or solvate thereof for use in therapy, and in particular in the treatment of human or animal subjects suffering from a condition in which there is an advantage in decreasing plasma free fatty acid concentration, or reducing heart rate and conduction, or whereby the therapy involves the treatment of ischaemic heart disease, peripheral vascular disease or stroke or which subject is suffering from a CNS disorder, sleep apnoea or pain.

In a further aspect, the invention provides a method of treatment of a human or animal subject suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering a CNS disorder or suffering from sleep apnoea or suffering pain, which method comprises administering to the subject an effective amount of a compound of formula (I) or a pharmaceutically acceptable salt or solvate thereof.

In respect of the above mentioned ischaemic treatment, it has been found that according to a particularly unexpected aspect of the present invention, not only does administration of a compound of formula (I) prior to ischaemia provide protection against myocardial infarction, but protection is also afforded if the compound of formula (I) is administered after the ischaemic event and before reperfusion. This means that the methods of the present invention are applicable not only where ischaemia is planned or expected, for example in cardiac surgery, but also in cases of sudden or unexpected ischaemia, for example in heart attack and unstable angina.

It will be appreciated that reference to treatment includes acute treatment or prophylaxis as well as the alleviation of established symptoms.

In yet a further aspect, the invention provides a pharmaceutical composition comprising at least one compound of formula (I) or a pharmaceutically acceptable salt or solvate thereof in association with a pharmaceutical carrier and/or excipient.

In another aspect, the invention provides a pharmaceutical composition comprising, as active ingredient, at least one compound of formula (I) or a pharmaceutically acceptable salt or solvate thereof in association with a pharmaceutical carrier and/or excipient for use in therapy, and in particular in the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease or stroke, or which subject is suffering from a CNS disorder, sleep apnoea or pain.

There is further provided by the present invention a process of preparing a pharmaceutical composition, which process comprises mixing at least one compound of formula (I) or a pharmaceutically acceptable salt or solvate thereof, together with a pharmaceutically acceptable carrier and/or excipient.

Compositions according to the invention may be formulated for topical, oral, buccal, parenteral or rectal administration or in a form suitable for administration by inhalation or insufflation. Oral administration is preferred. The compositions may be adapted for sustained release.

For topical administration, the pharmaceutical composition may be conveniently given in the form of a transdermal patch.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, or carboxymethyl cellulose; emulsifying agents, for example, sorbitan mono-oleate; non-aqueous vehicles (which may include edible oils), for example, propylene glycol or ethyl alcohol; and preservatives, for example, methyl or propyl p-hydroxybenzoates or sorbic acid. The preparations may also contain buffer salts, flavouring, colouring and sweetening agents (e.g. mannitol) as appropriate.

For buccal administration the compositions may take the form of tablets or lozenges formulated in conventional manner.

The compounds of formula (I) may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of formula (I) may also be formulated as suppositories, e.g. containing conventional suppository bases such as cocoa butter or other glycerides.

A proposed dose of the compounds of the invention for administration to man (of approximately 70 kg body weight) is 1 mg to 2 g, preferably 1 mg to 100 mg, of the active ingredient per unit dose which could be administered, for example, 1 to 4 times per day. It will be appreciated that it may be necessary to make routine variations to the dosage, depending on the age and condition of the patient. The dosage will also depend on the route of administration.

In a yet further aspect the invention also provides for the use of a compound of formula (I) or a pharmaceutically acceptable salt or solvate thereof for the manufacture of a medicament for the treatment of human or animal subjects suffering from a condition in which there is an advantage in decreasing plasma free fatty acid concentration, or reducing heart rate and conduction, or which subject is suffering from or susceptible to ischaemic heart disease, peripheral vascular disease (PVD) or stroke, or which patient is suffering from a CNS disorder, sleep apnoea or pain.

The compounds of formula (I) and physiologically acceptable salts or solvates thereof may be prepared by the processes described hereinafter, said processes constituting a further aspect of the invention. In the following description, the groups $R^1$, $R^2$ and $R^3$ are as defined for compounds of formula (I) unless otherwise stated.

According to a first general process (A), a compound of formula (I) may be prepared by reacting a compound of formula (II).

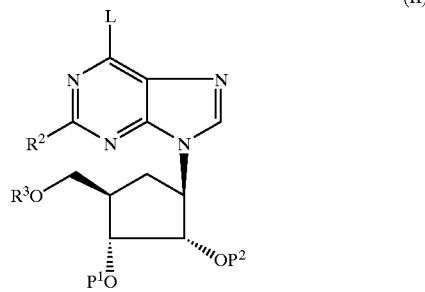

(II)

wherein, L represents a leaving group such as a halogen atom (e.g. a chlorine atom) and $P^1$ and $P^2$ represent hydrogen or a suitable protecting group (e.g. acetyl). with a compound of formula $R^1NH_2$ or a salt thereof, under basic conditions.

Compounds of formula (II) may be used to produce compounds of formula (I) directly by reaction with the group $R^1NH_2$ either in the absence or presence of a solvent such as an alcohol (e.g. a lower alkanol such as isopropanol, t-butanol or 3-pentanol), an ether (e.g. tetrahydrofuran or dioxan), a substituted amide (e.g. dimethylformamide), a halogenated hydrocarbon (e.g. chloroform) or acetonitrile, preferably at an elevated temperature (e.g. up to the reflux temperature of the solvent), in the presence of a suitable acid scavenger, for example, inorganic bases such as sodium or potassium carbonate, or organic bases such as triethylamine, diisopropylethylamine or pyridine.

This reaction may be preceded or followed where appropriate by in situ removal of the $P^1$ and $P^2$ protecting groups. For example when $P^1$ and $P^2$ represent acetyl, this may be effected with an amine such as ammonia or tert-butylamine in a solvent such as methanol.

Compounds of formula (II) may be prepared by the reaction of a compound of formula (III).

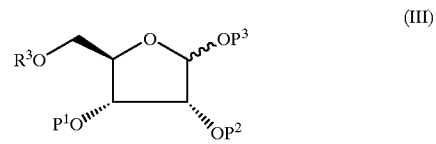

(III)

wherein $p^3$ represents a suitable protecting group for example $C_{1-3}$alkyl or acetyl, and $P^1$, $P^2$ and $R^3$ are as defined above, with a compound of formula (IV)

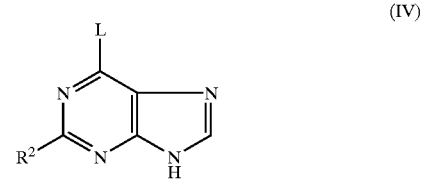

(IV)

wherein L and $R^2$ are as defined above.

The reaction is conveniently carried out in a suitable solvent, such as acetonitrile in the presence of a silylating agent such as trimethylsilyl trifluoromethane sulfonate and a base such as diazabicyclo [5.4.0]undec-7-ene (DBU). Alternatively the compound of formula (IV) may first be silylated with a suitable silylating agent e.g. hexamethyidisilazane followed by reaction of the silylated intermediate with a compound of formula (III) and a suitable Lewis acid, e.g. trimethylsilyl trifluoromethane sulfonate in a suitable solvent such as acetronitrile.

Compounds of formula (IV) are either known in the art or may be prepared from known compounds using methods analogous to those used to prepare the known compounds of formula (IV).

Compounds of formula (III) may be prepared from alternative protected compounds by replacement of the alternate protecting groups with $P^1$ and $P^2$, for example when $P^1$ and $P^2$ represent acetyl, compounds of formula (III) may be prepared from compounds of formula (V), wherein $P^4$ and $P^5$ represent $C_{1-3}$ alkyl and $P^3$ is as defined above, by acid catalysed removal of the alkylidine protecting group, e.g. with hydrogen chloride in methanol, followed by in situ acylation for example with acetic anhydride in the presence of a base such as pyridine, in a solvent such as dichloromethane.

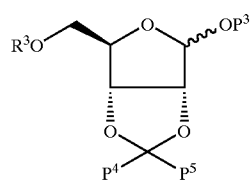
(V)

Compounds of formula (V) are known compounds or prepared by methods analogous to those used in the art to prepare the known compounds of formula V. It will be appreciated by a skilled person that the acetyl group in any of the compounds above could be replaced with any suitable protecting group, for example, other esters.

By analogous methods, compounds of formula (I) or (II) may also be prepared from compounds wherein alkylidine groups defined by $P^4$ and $P^5$ replace $P^1$ an $P^2$. This reaction represents an exchange of one protecting group for another and such reactions will be apparent to a person skilled in the art.

A further process (B) comprises converting a compound of formula (I) into a different compound of formula (I) by modifying the $R^1$, $R^2$ or $R^3$ group therein.

Certain compounds of formulae (II), (III), (IV), and (V) are novel intermediates and form a further aspect of the present invention.

Compounds of the formula $R^1NH_2$ are either known compounds or may be prepared from known compounds using conventional procedures.

Specific optical isomers of a compound of formula (I) may be obtained by conventional methods for example, by synthesis from an appropriate asymmetric starting material using any of the processes described herein, or where appropriate by separation of a mixture of isomers of a compound of formula (I) by conventional means e.g by fractional crystallisation or chromatography.

In the general processes described above, the compound of formula (I) obtained may be in the form of a salt, conveniently into the form of a pharmaceutically acceptable salt. Where desired, such salts may be converted into the corresponding free bases using conventional methods.

Pharmaceutically acceptable acid addition salts of the compounds of formula (I) may be prepared by reacting a compound of formula (I) with an appropriate acid in the presence of a suitable solvent such as acetonitrile, acetone, chloroform, ethyl acetate or an alcohol (e.g. methanol, ethanol or isopropanol). Pharmaceutically acceptable base addition salts may be obtained in an analogous manner by treating a solution of a compound of formula (I) with a suitable base. Pharmaceutically acceptable salts may also be prepared from other salts, including other pharmaceutically acceptable salts of the compounds of formula (I), using conventional methods.

The invention is further illustrated by the following non-limiting Intermediates and Examples. Temperatures are in ° C.

Standard HPLC conditions are as follows:

Standard Automated Preparative HPLC Column, Conditions & Eluent

Automated preparative high performance liquid chromatography (autoprep. HPLC) was carried out using a Supelco ABZ+5 μm 100 mm×22 mm i.d. column eluted with a mixture of solvents consisting of i) 0.1% formic acid in water and ii) 0.05% formic acid in acetonitrile, the eluant being expressed as the percentage of ii) in the solvent mixture, at a flow rate of 4 ml per minute. Unless otherwise stated the eluent was used as a gradient of 0–95% (ii) over 20 minutes.

LC/MS System (5.5 min Run Time)

This system used an ABZ+PLUS, 3.3 cm×4.6 mm i.d. column, eluting with solvents: A—0.1%v/v formic acid; and B—95:5 acetonitrile:water+0.07%v/v formic acid, at a flow rate of 1.5 ml per minute. The following gradient protocol was used: 100% A for 0.2 mins; A+B mixtures, gradient profile 0–100% B over 3.5 mins; hold at 100% B for 1 min; return to 100% A over 0.2 mins. The system used a micromass 'plaftform' spectrometer, with electrospray ionisation mode, positive and negative ion switching, mass range 80–1000 a.m.u.

HPLC System

The analytical HPLC system used a BDS-C18 5μ 5591 column, eluting with acetonitrile/water starting at 30% acetoniltrile/water increasing to 60% acetonitrile over 10 mins with a flow rate of 1.0 mL/min. This system used a diode array detector monitoring at a wavelength of 226 nm UV.

Flash chromatography was carried out over Merck silica gel (Merck 9385), or Merck alumina (Merck 1077).

Intermediate 1

Acetic Acid 4R-Acetoxy-5-methoxy-2R-methoxymethyl-tetrahydro-furan-3R-yl Ester

Acetyl chloride (29.4 ml) was added to methanol (1806 ml), (3aR,4R,6R,6aR)-4-methoxy-6-methoxymethyl-2,2-dimethyl-tetrahydro-furo[3,4-d][1,3]dioxole [Gudmundsson et al; J Med. Chem. (1997) 40(S), 785–793] (90.3g) was added, and the mixture was heated under reflux for 5 days, during which time methanol was continuously distilled off and replaced with fresh methanol in order to drive the reaction near to completion. Pyridine (117 ml) was added, and the methanol was replaced by ethyl acetate by distilling off the solvent and replacing with ethyl acetate until the solvent was distilling at 76°. The volume was reduced to 400 ml, the mixture cooled to 22°, acetic anhydride (136 ml) added, and the mixture was stirred at 22° for 16 h. The mixture was poured into saturated aqueous sodium bicarbonate (500 ml), and solid sodium bicarbonate was added until pH>7 was obtained. After stirring for 30 min, the aqueous layer was separated and further extracted with ethyl acetate. The combined organic layers were dried ($MgSO_4$), evaporated in vacuo, and azeotroped with toluene. Distillation at 0.042 mbar gave the title compound as a colourless oil (43.6 g).

TLC $SiO_2$ [isohexane:ethyl acetate 1:1] 2 spots (α and β anomers), Rf=0.6, 0.7.

Intermediate 2

Acetic acid 4R-Acetoxy-2R-(6-chloro-purin-9-yl)-5R-methoxymethyl-tetrahydrofuran-3R-yl Ester 6-Chloropurine (3.53 g), 1,1,1,3,3,3-hexamethyidisilazane (12 ml) and toluene (40 ml) were heated under reflux under nitrogen for 105 min. The solvent was removed in vacuo. The residue was taken into dry acetonitrile (50 ml) and treated with acetic acid 4R-acetoxy-5-methoxy-2R-methoxymethyl-tetrahydrofuran-3R-yl ester (2.00 g) and trimethylsilyl trifluoromethanesulfonate (1.9 ml) then heated under reflux for 4.5 h. The resulting solution was cooled to 20°, poured into 8% sodium bicarbonate solution and extracted with ethyl acetate. The organic extracts were dried (MgSO$_4$) and evaporated in vacuo and the residue purified by flash chromatography on silica gel, eluting with cyclohexaneethyl acetate (5:1–3:1 gradient) to afford the title compound (2.3 g).

Mass spectrum m/z 385 (MH$^+$).

Intermediate 3

6-Chloro-9-(6R-methoxymethyl-2,2-dimethyl-tetrahydro-(3aR,6aR)-furo[3,4-d][1,3]dioxol-4R-yl)-9H-purine 6-Chloro-9-[2,3-O-(1-methylethylidene)-β-D-ribofuranosyl]-9H-purine [H Guilford, PO Larsson, K Mosbach, Chem. Scr., 1972, 2(4), 165–170] (6.0 g) was dissolved in dry dioxan (150 mL) and sodium hydride (60% oil dispersion, 0.75 g) added in portions over 10 mins at room temperature. The mixture was stirred for 0.5 h and dry benzyltriethylammonium chloride (1.5 g) added. After a further 0.25 h, dimethylsulphate (3 mL; 4.0 g; 31.6 mmol) was added and stirring continued overnight to give a slightly cloudy solution. After a total of 24 h, acetic acid (1.5 mL) was added and the solution evaporated to dryness and the residual oil partitioned between water and ethyl acetate. The combined organic phases were dried and concentrated in-vacuo. The residue purified by flash chromatography on silica gel, eluting with cyclohexane-ethyl acetate (1:1) to afford the title compound as a colourless oil, (2.5 g).

TLC SiO$_2$ [EtOAc: cyclohexane: 2:1] Rf=0.50.

Intermediate 3 (Alternative Method)

6-Chloro-9-(6R-methoxymethyl-2,2-dimethyl-tetrahydro-(3aR,6aR)-furo[3,4d][1,3]dioxol-4R-yl)-9H-purine A mixture of 6-chloro-9-[2,3-O-(1-methylethylidene)-β-D-ribofuranosyl]-9H-purine (0.50 g), silver (I) oxide (0.40 g) and methyl iodide (10 mL) in acetone (10 mL) were stirred at reflux for 4 h then left at room temperature for 40 h. The mixture was returned to reflux for 6 h and then left to cool to room temp for 16 h. The precipitate was filtered through hyflo and the filtrate concentrated in-vacuo then purified by flash chromatography on silica gel, eluting with cyclohexane-ethyl acetate (2:1 to 1:1) to afford the title compound as a colourless oil (151 mg).

TLC SiO$_2$ [EtOAc: cyclohexane: 1:11]Rf=0.2.

Intermediate 4

(2R,3R,4 S,5 R)-2-(6-Chloro-purin-9-yl)-5-methoxymethyl-tetrahydro-furan-3,4 diol Cold trifluoroacetic acid (6 ml) was added to the 6-chloro-9-(6R-methoxymethyl-2,2-dimethyl-tetrahydro-(3aR,6aR)-furo[3,4-d][1,3dioxol-4R-yl)-9H-purine, (1,5 g) cooled in ice. Water (0.6 ml) was added and the mixture stirred at 4° for 3 h. The cold solution was added in portions to cold 8% sodium bicarbonate (40 ml) and the mixture basified by adding solid sodium bicarbonate. The mixture was extracted with ethyl acetate and the extracts dried and concentrated in-vacuo to give the title compound as a white foam (1.3 g; 98%).

Tlc SiO$_2$ [EtOAc: cyclohexane 1:2] Rf=0.20.

Intermediate 5

(1R,2R)-2-[9-(6R-Methoxymethyl-2,2-dimethyl-tetrahydro-(3aR,6aR)-furo[3,4-d][1,3]dioxol-4R-yl)-9H-purin-6-ylamino]-cyclopentanol A solution of 6-chloro-9-(6R-methoxymethyl-2,2-dimethyl-tetrahydro-(3aR,6aR)-furo[3,4-d][1,3][1,3]doxol-4R-yl)-9H-purine (350 mg,), (1R,trans)-2-hydroxycyclopentylamine hydrochloride (155 mg) and N,N-diisopropylethylamine (0.61 ml) in isopropanol (5 ml) was stirred at reflux under nitrogen for 18 h. The reaction mixture was concentrated in-vacuo and the residue was purified by flash chromatography on silica gel, eluting with tolueune:ethanol: triethylamine (90:10:1) to give a white foam (395 mg).

TLC SiO$_2$ [toluene:ethanol:triethylamine 90:10:1] Rf=0.41.

Intermediate 6

4-[9-(6R-Methoxymethyl-2,2-dimethyl-tetrahydro-(3aR,6aR)-furo[3,4-d][1,3]dioxol-9H-purin-6-ylamino]-benzioc Acid Methyl Ester A solution of 6-chloro-9-(6R-methoxymethyl-2,2-dimethyl-tetrahydro-(3aR,6aR)-furo[3,4-d][1,3]dioxol-4R-yl)-9H-purine (1.0 g), methyl 4-aminobenzoate (1.11 g) and N,N-diisopropylethylamine (1.54 mL) in isopropanol (25 mL) was stirred at reflux under nitrogen. Two further portions of diisopropylethylamine (1.03 mL) were added after 6 days and 13 days. After a total of 17 days the solution was concentrated and purified by flash chromatography on silica gel, eluting with ethyl acetate:cyclohexane (1:2). This gave the title compound as a white foam (668 mg).

TLC SiO$_2$ [EtOAc:cyclohexane 1:2] Rf=0.11.

Intermediate 7

{4-[9-(6R-Methoxymethyl-2,2-dimethyl-tetrahydro-(3aR,6aR)-furo[3,4-d][]1,3]dioxol-9H-purin-6-ylamino]phenyl}-methanol A solution of 4-[9-(6R-methoxymethyl-2,2-dimethyl-tetrahydro-(3aR,6aR)-furo[3,4-d][]1,3]dioxol-4R-yl-9H-purin-6-ylamino]-benzioc acid methyl ester (100 mg) in THF (5 ml) was added to a suspension of lithium aluminium hydride (10 mg) in THF (4 ml) under nitrogen. The resulting mixture was stirred at room temperature for 3 h. More lithium aluminium hydride (0.705 mmol) was added in 2 portions over 6 h. After a total of 21 h, the reaction mixture was quenched with water (0.05 ml), followed by sodium hydroxide solution (3N, 0.05 ml), then further addition of water (0.15 ml). The mixture was stirred for 1 h and the solid removed by filtration (hyflo) and washed with methanol. The filtrate and washings were concentrated in-vacuo to give a yellow solid. This was was purified by flash chromatography on silica gel, eluting with cyclohexane:ethyl acetate (1:9) to give the title compound as a yellow oil (33 mg).

TLC silica [EtOAc] Rf=0.30

Intermediate 8

Acetic acid 4R-Acetoxy-2R-(6-chloro-2-methyl-purin-9-yl)-5R-methoxymethyl-tetrahydro-furan-3R-yl ester.

6-Chloro-2-methyl-9H-purine hydrochloride[Robins et al; J. Org. Chem, 1956, 21, 695–696] (18.4 g) was added at 20° to a stirred solution of acetic acid 4-Racetoxy-5-methoxy-2R-methoxymethyl-tetrahydro-furan-3R-yl ester (intermediate 1) (20.0 g) in acetonitrile (200 ml). 1,8-Diazabicyclo [5.4.0] undec-7-ene (DBU) (34.2 ml) was added in 2 portions, maintaining the temperature at 15±5°. After stirring for 5 min at 20°, trimethylsilyl trifluoromethanesulphonate (73.7 ml) was added dropwise over 3 min, maintaining the temperature at 20°. The mixture was warmed to 60° for 2 h, and transferred via cannula into water (400 ml) containing potassium carbonate (84 g). The mixture was extracted with ethyl acetate (4×100 ml), and the organic layers were washed with 0.5M hydrochloric acid (200 ml) and aqueous potassium carbonate, dried ($MgSO_4$), and evaporated in vacuo. The oily residue was purified by chromatography on silica gel, eluting with ethyl acetate, and by recrystallisation from ethyl acetate to give the title compound (16.5 g).

TLC $SiO_2$ [Ethyl acetate: cyclohexane 1:1] Rf=0.2;

Mass Spectrum m/z 399 [$MH^+$].

Intermediate 9

2,5'-O-Dimethyl-2',3'-O-(1-methylethylidene)inosine

A solution of 2-methyl-2',3'-(1-methylethylidene)inosine [A Yamazaki et al., J. Org.Chem. 1967, 32, 3258] (4.0 g) in dry dimethylformamide (31 ml) was added dropwise to an ice-cooled suspension of sodium hydride (60% dispersion in oil, 1.09 g) in dry dimethylformamide (8 ml). The resulting suspension was stirred at room temperature for 2 hours, recooled to 0° and treated with iodomethane (0.82 ml). The reaction mixture was stirred at room temperature for 20 hours, acetic acid (1.54 ml) was added and stirring was continued for a further 24 hours. The solvent was removed under vacuum and the residue was purified by flash chromatography on a silica column eluting with dichloromethane/methanol/ammonia (97:3:0.5 changing to 95:5:0.5) to give the title compound (1.16 g) as a light brown foam.

T.l.c. $SiO_2$ [dichloromethane/methanol/ammonia 90:10:1] Rf=0.38.

Intermediate 10

1-(6-Chloro-2-methyl-9H-purin-9-yl)-1-deoxy-5-O-methyl-2,3-O-(1-methylethylidene)-β-D-ribofuranose Phosphorus oxychloride (0.8 ml) was added to a mixture of Intermediate 9 (1.16 g) and 4-dimethylaminopyridine (462 mg) in dry acetonitrile (15 ml) which was then stirred at reflux for 2.75 hours. The cooled solution was concentrated under vacuum and the residue was basified using 2N sodium carbonate (75 ml). The aqueous mixture was extracted with ethyl acetate (x2) and the combined organic extracts were dried ($Na_2So_4$) and concentrated to a brown oil which was purified by flash chromatography on a silica column eluting with cyclohexane/ethyl acetate (1:1) to give the title compound (436 mg) as a colourless oil.

T.l.c. $SiO_2$ (cyclohexane/ethyl acetate 1:1) Rf=0.29.

Intermediate 11

1-(6-Chloro-2-methyl-9H-purin-9-yl)-1-deoxy-5-O-methyl-b-D-ribofuranose

Ice-cold Intermediate 2 (415 mg) was treated with an ice-cold mixture of trifluoroacetic acid (4.2 ml) and water (0.42 ml) and the reaction mixture was stirred at 0° for 1.5 hours. Excess trifluoroacetic acid was removed under vacuum and the residue was purified by flash chromatography on a silica column (Merck 9385, dichloromethane/methanol/ammonia 130:10:1) to give the title compound (276 mg) as a white solid.

T.l.c. silica (dichloromethane/methanol/ammonia 90:10:1) Rf 0.48.

In an alternative method intermediate 11 was synthesised by the following procedure. tert-Butylamine (3.5 ml) was added to a cooled suspension of acetic acid 4R-acetoxy-2R-(6-chloro-2-methyl-purin-9yl-5R-methoxymethl-tetrahydro-furan-3R-yl ester ('intermediate 8') (4.75 g) in methanol (53 ml), and the mixture was stirred at 0° for 1.5 h. The mixture was filtered, and the residue washed with methanol and dried in vacuo at 50° to give the title compound as a white powder (0.9 g). Concentration of the mother liquors in vacuo and trituration of the residue with diisopropyl ether (25 ml) gave further title compound (2.6 g) as a white powder.

EXAMPLE 1

5'-O-Methyl-N-(tetrahydro-furan-3R-yl)-adenosine

A mixture of (2R,3R,4S,5R)-2-(6-chloro-purin-9-yl)-5-methoxymethyl-tetrahydrofuran-3,4(125 mg), (3R)-3-aminotetrahydrofuran hydrochloride (62 mg), N,N-diisopropylethylamine (0.27 ml) and isopropanol (5 ml) was heated at reflux for 24 h and then cooled to room temperature. Silica (Merck 7734) was added and the mixture concentrated in vacuo. The solid residue was purified by flash chromatography on silica gel, eluting with ethyl acetate: methanol (19:1). The resulting white solid was recrystallised from ethyl acetate to provide the title compound as a white powder (90 mg).

Analysis Found: C, 50.3; H, 5.9; N, 19.5. $C_{15}H_{21}N_5O_5$.0.3 $H_2O$ requires: C, 50.5; H, 6.1; N, 19.6%. mp=179–180° C.

The following examples were all prepared from Intermediate 4 by analogous methods to Example 1, using reaction times and stoichiometry depending on the reactivity of the amine.

EXAMPLE 2

5'-O-Methyl-N-(tetrahydro-pyran-4-yl)-adenosine

Analysis Found: C, 52.7; H, 6.5; N, 18.9. $C_{16}H_{23}N_5O_5$. requires: C, 52.6; H, 6.3; N, 19.2%. mp 133–134° C.

EXAMPLE 3

N-(2S-Methoxy-(S)-cyclopentyl)-5'-O-methyl-adenosine

Analysis Found: C, 53.1; H, 6.7; N, 18.3. $C_{17}H_{25}N_5O_5$.0.25 $H_2O$ requires: C, 53.2; H, 6.7; N, 18.2%. Nmr in $d_6$-DMSO 8.36δ (1H, s, CH), 8.26δ (1H, brs, CH), 7.81δ (1H, brd, NH), 5.96δ (1H, d, CH), 5.6δ (1H, brd, OH), 5.37δ (1H, brd, OH), 4.7–4.55δ (2H, brm, 2×CH), 4.18δ (1H, brm, CH), 4.05δ (1H, m, CH), 3.85δ (1H, m, CH), 3.6δ (2H, m, $CH_2$), 3.33δ (3H, s, OMe), 3.28δ (3H, s, OMe), 2.1–1.5δ (6H, 2×m, 3×$CH_2$).

EXAMPLE 4

5'-O-Methyl-N-(2S-methyl-tetrahydro-furan-3R-yl)-adenosine

TLC $SiO_2$[EtOAc: MeOH 9:1] Rf=0.30; mp=156–159° C.

EXAMPLE 5

N-(3-Chloro4-hydroxy-phenyl)-5'-O-methyl-adenosine mp=225–230 ° C. LC/MS: $R_t$=2.45 min; Mass spectrum m/z 408 (MH$^+$)

EXAMPLE 6

5'-O-Methyl-N-(1R-methyl-2-phenyl-ethyl)-adenosine

Analysis Found: C, 58.5; H, 6.3; N, 17.0. $C_{20}H_{25}N_5O_4$. 0.6 $H_{20}$ requires: C, 58.6; H, 6.4; N, 17.1%. LC/MS: $R_t$=2.63 min; Mass spectrum m/z 400 (MH$^+$).

EXAMPLE 7

5'-O-Methyl-N-[4-(2-methyl-2H-tetrazol-5-yl)-phenyl]adenosine

LC/MS: $R_t$=2.57 min; Mass spectrum m/z 440 (MH$^+$).

EXAMPLE 8

3-{4-[9-(3R,4S-Dihydroxy-5R-methoxymethyl-tetrahydro-furan-2R-yl)-9H-purin-6-ylamino]-phenyl}-(E)-acrylic Acid TLC SiO$_2$[CH$_2$Cl$_2$: EtOH: 880NH$_3$5:8:1] Rf=0.15; mp=257–263° C.

EXAMPLE 9

{4-[9-(3R,4S-Dihydroxy-5R-methoxymethyl-tetrahydro-furan-2R-yl)-9H-purin-6-ylamino]-phenoxy}-acetic Acid Analysis Found: C, 48.9; H, 4.6; N, 14.9. $C_{19}H_{21}N_5O_7$. requires: C, 48.8; H, 5.4; N, 15.0%. mp=210–215° C.

EXAMPLE 10

5-[9-(3R,4S-Dihydroxy-5R-methoxymethyl-tetrahydro-furan-2R-yl)-9H-purin-6-ylamino]-benzofuran-2-carboxylic Acid Methyl Ester LC/MS: $R_t$=2.67 min; Mass spectrum m/z 456 (MH$^+$).

EXAMPLE 11

5'-O-Methyl-N-(tetrahydro-thiopyran-4-yl)-adenosine

Analysis Found: C, 49.8; H, 6.2; N, 18.0; S, 8.4. $C_{16}H_{23}N_5O_4S$. 0.25 H$_2$O; requires: C, 49.8; H, 6.1; N, 18.1; S 8.3%. TLC SiO$_2$[EtOAc: MeOH:19:1] Rf=0.46.

EXAMPLE 12

N-rel-[(1R,5R)-Bicyclo[3.2.0]hept-6S-yl]-5'-O-methyl-adenosine

TLC SiO$_2$[EtOAc: MeOH: 30:1] Rf=0.21; Analysis Found: C, 56.4; H, 6.9; N, 17.5. $C_{18}H_{25}N_5O_4$. 0.05 H$_2$O . 0.2$^i$PrOH; requires: C, 56.4; H, 7.0; N, 17.7%.

EXAMPLE 13

5'-O-Methyl-N-(1S-methoxymethyl-2-methyl-propyl)-adenosine

TLC SiO$_2$[CH$_2$Cl$_2$: MeOH: 880NH$_3$120:8:1] Rf=0.30; Nmr d$_6$-DMSO 8.33δ (1H, brs, CH) 8.25–8.10δ (1H, 2×brs, CH) 7.45δ (1H, brd, NH), 5.92δ (1H, d, CH) 5.55δ (1H, brd, OH) 5.3δ (1H, brd, OH) 5.1,4.4δ (1H, 2×brs, CH) 4.62δ (1H, brs, CH) 4.18δ (1H, m, CH) 4.02δ (1H, m, CH) 3.5–3.2δ (11H, m+3×s, CH+2×CH$_2$+2×OCH$_3$) 1.95δ (1H, m, CH) 0.92δ (6H 2×CH$_3$).

EXAMPLE 14

N-(2-Hydroxy-1R-methyl-ethyl)-5'-O-methyl-adenosine

Analysis Found: C, 49.2; H, 6.2; N, 20.4. $C_{14}H_{21}N_5O_5$. requires: C, 49.6; H, 6.2; N, 20.6%. mp=232–233° C.

EXAMPLE 15

N-(2-Fluoro-1R-methyl-ethyl)-5'-O-methyl-adenosine

TLC SiO$_2$[EtOAc: MeOH 30:1] Rf=0.21; HPLC $R_t$=9.4 min.

EXAMPLE 16

N-(1S-Fluoromethyl-2-methoxy-ethyl)-5'-O-methyl-adenosine

TLC SiO$_2$[EtOAc: MeOH 30:1] Rf=0.16 HPLC $R_t$=10.0 min.

EXAMPLE 17

N-(2R-Hydroxy-(R)-cyclopentyl)-5'-O-methyl-adenosine (1R,2R)-2-[9-(6R-Methoxymethyl-2,2-dimethyl-tetrahydro-(3aR,6aR)-furo[3,4-d[]1,3]dioxol-4R-yl)-9H-purin-6-ylamino]-cyclopentanol (235 mg) was cooled in an ice-bath, then treated with ice-cold trifluoroacetic acid:water (10:1, 2.75 ml). After 1 h the solution was concentrated in-vacuo and the residue was purified by flash chromatography on silica gel, eluting with dichloromethane: methanol:ammonia 94:6:1, then 90:10:1. The crude product was triturated with warm ethyl acetate, then cold ether to give the title compound as a white solid (130 mg).

Analysis Found: C, 52.8; H, 6.6; N, 19.2. $C_{16}H_{23}N_5 O_5$ requires: C, 52.6; H, 6.3; N, 19.2%. mp=202–204 ° C.

EXAMPLE 18

N-(3-Amino-propyl)-5'-O-methyl-adenosine

This compound was prepared by analogous means to Example 17. Analysis Found: C, 45.6; H, 6.2; N, 21.6. $C_{20}H_{25}N_5O_4$. 1.7 H$_2$O requires: C, 45.6; H, 6.9; N, 22.7%.

LC/MS: $R_t$=1.69 min; Mass spectrum m/z 339 (MH$^+$).

EXAMPLE 19

N-tert-Butyl-5'-O-methyl-adenosine

Acetic acid 4R-acetoxy-2R-(6-chloro-purin-9-yl)-5R-methoxymethyl-tetrahydro-furan-3R-yl ester (1.15 g) was dissolved in methanol (15 ml), cooled to 0–5°, and tert-butylamine (10 ml) added. The solution was allowed to stand at 0–5° for 1 h, then evaporated to dryness in vacuo, to afford a white solid (0.99 g) which was purified by flash chromatography on silica gel, eluting with dichloromethane methanol (99:1–4:1) to afford intermediate 2 as a white solid and also the title compound as a white solid (44 mg).

Mass spectrum m/z 338 (MH$^+$); Nmr CDCl$_3$ 8.286 (1H, s, CH), 8.04δ (1H, s, CH), 6.5δ (1H, vbrs, OH), 6.0δ (1H, d, CH), 5.82δ (1H, brs, OH), 4.5–4.35δ (3H, m, 3 ×CH), 3.8–3.55δ (3H, brs+m, NH+CH$_2$), 3.385 (3H, s, OMe), 1.57δ (9H, s, t-But).

EXAMPLE 20

N-(2S-Fluoro-(S)-cyclopentyl)-5'-O-methyl-adenosine

Acetic acid 4R-acetoxy-2R-(6-chloro-purin-9-yl)-5R-methoxymethyl-tetrahydro-furan-3R-yl ester (50 mg), (1S, 2S)-2-fluorocyclopentylamine hydrochloride (71 mg) and diisopropylethylamine (0.4 ml) were heated at 80° in isopropanol (5 ml) in a reactivial for 17 h. The solution was evaporated under a stream of nitrogen and purified by autoprep HPLC to afford the title compound as a colourless solid (33 mg).

Mass spectrum m/z 368 (MH$^+$); Nmr d$_4$-MeOD 8.4δ (1H, s, CH), 8.3δ (1H, s, CH), 6.08δ (1H, d, CH), 5.05δ (1H, dm, CH, JF-CH 50 Hz), 4.70δ (1H, br, CH), 4.56δ (1H, t, CH), 4.32δ (1H, t, CH), 4.2δ (1H, m, CH), 3.69δ (2H, m, CH$_2$), 3.45 (3H, s, —OMe), 2.4–1.65 (6H, m, 3×CH$_2$).

The following were prepared from Intermediate 20 by analogous methods to Example 20.

EXAMPLE 21

N-(2,3-Dihydroxy-propylamino)-5'-O-methyl-adenosine

Mass spectrum m/z 356 (MH$^+$); Nmr d$_4$-MeOD 8.33δ (1H, s, CH), 8.26δ (1H, s, CH), 6.04δ (1H, d, CH), 4.65δ (1H, t, CH2), 4.34δ (1H, t, CH), 4.24δ (1H, q, CH), 3.94δ (1H, m, CH), 3.58–3.68δ (6H, m, 3×CH), 3.40δ (3H, s, —OMe).

EXAMPLE 22

N-rel-[(1S,4R)-Bicyclo[2.2.1]hept-2R-yl]-5'-O-methyl-adenosine

Mass spectrum m/z 376 (MH$^+$); Nmr d$_4$-MeOD 8.36δ (1H, brs, CH), 8.24δ (1H, s, CH), 6.04δ (1H, d, CH), 4.54δ (1H, t, CH), 4.42–4.20δ (2H, brs+t, 2×CH), 4.15δ (1H, m, CH), 3.64δ (2H, ddd, CH$_2$), 3.40δ (3H, s, —OMe), 2.60δ (1H, t, CH), 2.36–2.10δ (2H, m+t, 2×CH), 1.76–136 (6H, m, CH$_2$), 1.1δ (1H, ddd, CH).

EXAMPLE 23

4-[9-(3R,4S-Dihydroxy-5R-methoxymethyl-tetrahydro-furan-2R-yl)-9H-purin-6-ylamino]-piperidine-1-carboxylic Acid Ethyl Ester Mass spectrum m/z 437 (MH$^+$); Nmr d$_4$-MeOD 8.33δ (1H, s, CH), 8.25δ (1H, s, CH), 6.05δ (1H, d, CH), 4.58δ (1H, t, CH), 4.33δ (2H, t+brs, 2×CH), 4.15δ (3H, q+m, CH$_2$+CH), 3.7δ (2H, m CH$_2$), 3.45δ (3H, s, —OMe), 3.1δ (2H, brt, CH$_2$), 1.6δ (4 H, m, CH$_2$), 1.28δ (3H, t, CH$_3$).

EXAMPLE 24

N-(4-Hydroxymethyl-phenyl)-5'-O-methyl-adenosine

Cooled trifluoroacetic acid (4.0 ml) and water (0.4 ml) were added to ice-cold {4-[9-(6R-methoxymethyl-2,2-dimethyl-tetrahydro-(3aR,6aR)-furo[3,4-d][1,3]dioxol-4R-yl)-9H-purin-6-ylamino]-phenyl}-methanol (370 mg) and stirred for 1.5 h. This was then added dropwise to an ice-cold solution of sodium bicarbonate (8%, 40 ml) and further sodium bicarbonate was added until the pH remained at pH8 to 9. This was extracted with ethyl acetate, the organic layers combined, dried (Na$_2$SO$_4$) and concentrated to give a white solid (~300 mg). This was was purified by flash chromatography on silica gel, eluting with dichloromethane, methanol, 0.88 ammonia (923:70:7) to give the title compound as a white solid.

TLC SiO$_2$[Dichloromethane, methanol, 0.88 ammonia (923:70:7)] Rf=0.14; LC/MS: R$_t$=2.23 min; Mass spectrum m/z 338 (MH$^+$).

EXAMPLE 25

2-[9-(3R,4S-Dihydroxy-5R-methoxymethyl-tetrahydro-furan-2R-yl)-2-methyl-9H-purin-6-ylamino]-ethanesulfonic Acid Methylamide A mixture of 1-(6-chloro-2-methyl-9H-purin-9-yl)-1-deoxy-5-O-methyl-β-D-ribofuranose, (0.15 g) and 2-aminoethanesulfonic acid methylamide hydrochloride (0.13 g) in isopropanol (12 ml) containing diisopropylethylamine (0.3 mi) was stirred at 95° for 42 h under nitrogen. The solution was then cooled to room temperature and concentrated in vacuo to give a yellow gum (0.47 g) which was purified twice by flash chromatography on silica gel, eluting with dichloromethane :ethanol:ammonia (100:8:1–75:8:1) and dichloromethane:ethanol:ammonia (100:8:1) to give the title compound (52 mg) as a pale yellow solid.

Mass spectrum m/z 417 (MH$^+$); Analysis Found: C, 42.6; H, 5.6; N, 19.6. C$_{15}$H$_{24}$N$_6$O$_6$S. requires: C, 43.3; H, 5.8; N, 20.2%.

The following compounds were prepared from 1-(6-chloro-2-methyl-9H-purin-9yl)-1-deoxy-5-O-methyl-β-by analogous methods to Example 26.

EXAMPLE 26

4-[9-(3R,4S-Dihydroxy-5R-methoxymethyl-tetrahydro-furan-2R-yl)-2-methyl-9H-purin-6-ylamino]-piperidin-2-one TLC SiO$_2$[CH$_2$Cl$_2$: MeOH: 880NH$_3$ 94:6:1] Rf=0.05; LC/MS: R$_t$=1.95 min; Mass spectrum m/z 393 (MH$^+$).

EXAMPLE 27

N-Cyclopentyl-2-methyl-5'-O-methyl-adenosine

TLC SiO$_2$[CH$_2$Cl$_2$: MeOH: 880NH$_3$ 94:6:1] Rf=0.21; LC/MS: R$_t$=2.28 min; Mass spectrum m/z 364 (MH$^+$).

EXAMPLE 28

N-Cyclopropyimethyl-2-methyl-5'-O-methyl-adenosine

Acetic acid 4R-acetoxy-2R-(6-chloro-2-methyl-purin-9-yl)-5R-methoxymethyltetrahydro-furan-3R-yl ester (50 mg), cyclopropylmethylamine (0.043 ml) and diisopropylethylamine (0.13 ml) were heated to reflux in isopropanol (5 ml) for 120 h. On cooling to room temperature, methanolic ammonia (4 ml) was added to the reaction mixture, shaken and left to stand for 1 day. The solvent was evaporated under a stream of nitrogen, and the residue purified by solid phase extraction (5 g Varian Bondelut carbridge, aminopropyl bonded phase) to give the title compound (32 mg) as a white solid.

Mass spectrum m/z 350 (MH$^+$); Nmr d$_4$-MeOD 8.25δ (1H, s, CH), 6.08δ (1H, d, CH), 4.57δ (1H, t, CH), 4.34δ (1H, t, CH), 4.2δ (1H, m, CH), 3.7δ (2H, m, CH$_2$), 3.48δ (5H, m+s, CH$_2$+OMe), 2.5δ (3H, s, —CH$_3$), 1.2δ (1H, m, CH), 0.65–0.28δ (4H, 2×m, 2×CH$_2$).

Reporter Gene Experiments

Agonist activity was measured in Chinese hamster ovary (CHO) cells containing the CRE/SPAP/HYG (CRE=cyclic AMP response element; HYG=hygromycin; SPAP=secreted placental alkaline phosphatase) reporter gene, which upon stimulation of cAMP levels produced SPAP. A cell line was used, which stably co-expresses the human adenosine A1 receptor. Cells were plated out in 96-well plates in culture medium and incubated at 37° C. for 1 hour. For measurement of potency, agonists were added to the appropriate wells at a concentration range of approximately $10^{-31\ 10}$–$10^{-5}$M. 15 Min later, cAMP levels were stimulated by addition of a maximal concentration of forskolin. All cells were then incubated for a further 5 hours at 37° C., and cooled to room temperature, after which a substrate for the phosphatase (para-nitrophenol phosphate, pNPP), which is broken down to a coloured reagent) was then added and the 96-well plates are read in a plate reader. From these readings, the concentration-dependence of the inhibition by the agonist of forskolin-stimulated SPAP production, can be calculated. One of the agonists tested on each 96-well plate was the standard non-selective agonist, N-ethylcarboxamidoadenosine (NECA), and the potency of all test agonists is expressed relative to that of the NECA standard.

(ECR=equipotent concentration ratio relative to NECA=1).

Results

TABLE 1

Biological Data. A1, A3 Receptor Gene Assay ECR

| Example | A1 | A3 |
|---|---|---|
| 1 | 2.70 | >129 |
| 2 | 3.30 | 180 |
| 3 | 1.01 | 204 |
| 4 | 0.90 | 338 |
| 5 | 6.21 | >116 |
| 6 | 1.27 | 5.00 |
| 17 | 3.90 | 57.3 |
| 19 | 1.62 | >243 |
| 20 | 1.38 | 54.8 |
| 21 | 1.77 | 135 |
| 22 | 0.39 | 112 |
| 23 | 2.20 | 162 |
| 25 | 1.67 | >288 |
| 27 | 3.02 | >263 |
| 28 | 8.07 | >99 |

We claim:

1. A compound of formula (I)

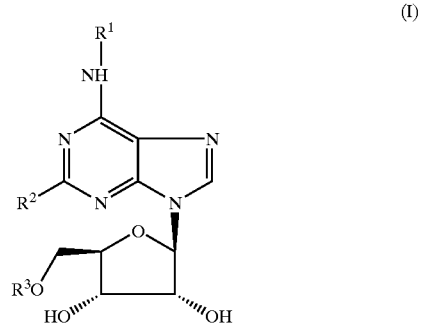

wherein R$^2$ represents C$_{1-3}$alkyl, halogen or hydrogen;
R$^3$ represents straight or branched alkyl group of 1–6 carbon atoms;
R$^1$ represents a group selected from the group consisting of:
(1) a fused bicyclic aromatic ring:

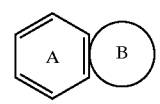

wherein B represents an aromatic mono-cyclic ring system comprising 5 or 6 carbon atoms wherein one or more of the carbon atoms is/are replaced by heteroatoms independently selected from nitrogen, oxygen and sulfur, wherein the bicyclic ring is attached to the nitrogen atom of formula (I) via a ring atom of ring A, and ring B is optionally substituted by —CO$_2$(C$_{1-3}$ alkyl);
(2) a phenyl group optionally substituted by one or more substituents selected from the group consisting of:
-halogen, —SO$_3$H, -(alk)$_n$OH, -(alk)$_n$-cyano, —(O)$_n$—C$_{1-6}$-alkyl (optionally subsituted by one or more halogens), -(alk)$_n$-nitro, —(O)$_m$-(alk)$_n$—CO$_2$R$^c$, -(alk$_n$) —CONR$^c$R$^d$, -(alk)$_n$ COR$^c$, -(alk)$_n$ SOR$^e$, -(alk)$_n$—SO$_2$R$^e$, -(alk)$_n$ SO$_2$NR$^c$R$^d$, -(alk)$_n$ OR$^c$, -(alk)$_n$(CO)$_m$ NHSO$_2$R$^e$, -(alk)$_n$—NHCOR$^c$, and -(alk)$_n$—NR$^c$R$^d$ wherein m and n are 0 or 1 and alk represents a C$_{1-6}$ alkylene group or C$_{2-6}$ alkenyl group;
(3) a phenyl group substituted by an aromatic mono-cyclic ring system comprising 5 or 6 carbon atoms wherein one or more of the carbon atoms is/are replaced by heteroatoms independently selected from nitrogen, oxygen and sulfur, said aromatic ring system optionally being substituted by C$_{1-3}$alkyl or NR$^c$R$^d$; wherein
R$^c$ and R$^d$ may each independently represent hydrogen, or C$_{1-3}$ alkyl or when part of a group NR$^c$R$^d$, R$^c$ and R$^d$ together with the nitrogen atom may form a 5 or 6 membered heterocyclic ring optionally containing other heteroatoms which heterocyclic ring may optionally be substituted further by one or more C$_{1-3}$ alkyl groups;
R$^e$ represents C$_{1-3}$ alkyl;
and physiologically acceptable solvates and salts thereof; with the proviso that, when R$^3$ represents C$_{1-6}$ alkyl, and R$^2$ represents C$_{1-3}$ alkyl, then R$^1$ cannot represent phenyl optionally substituted by one or more substituents selected from the group consisting of halogen, $C_{1-3}$alkyl, trifluoromethyl, nitro, cyano, —$CO_2R^c$, —$CONR^cR^d$, —$COR^c$, —$SOR^e$, —$SO_2R^e$, —$SO_2R^e$, —$SO_3H$, —$SO_2NR^cR^d$, —$OR^c$, —$NHSO_2R^e$, —$NHCOR^c$ and —$NR^cR^d$ with the further proviso that $N^6$-(3-chloro-4-hydroxy-phenyl)-5'-O-methyl-adenosine is excluded from this claim.

2. The compound according to claim 1 wherein $R^3$ represents $C_{1-3}$ alkyl.

3. The compound according to claim 2 wherein $R^3$ represents methyl or ethyl.

4. The compound according to claim 3 wherein $R^3$ represents methyl.

5. The compound according to claim 1 wherein $R^2$ represents hydrogen, methyl or halogen.

6. The compound according to claim 5 wherein $R^2$ represents hydrogen or methyl.

7. The compound according to claim 1 selected from the group consisting of:

5-[9-(3R,4S-dihydroxy-5R-methoxymethyl-tetrahydrofuran-2R-yl)-9H-purin-6-ylamino]-benzofuran-2-carboxylic acid methyl ester);

5'-O-methyl-$N^6$-[4-(2-methyl-2H-tetrazol-5-yl)-phenyl]-adenosine;

$N^6$-(4-hydroxymethyl-phenyl)-5'-O-methyl-adenosine;

(3-{4-[9-(3R,4S-dihydroxy-5R-methoxymethyltetrahydrofuran-2R-yl)-9H-purin-6-ylamino]phenyl}-(E)-acrylic acid; and {4-[9-(3R,4S-dihydroxy-5R-methoxymethyltetrahydrofuran-2R-yl)-9H-purin-6-ylamino]phenoxy}-acetic acid.

8. The compound according to claim 1 wherein $R^1$ represents a phenyl group substituted by one or more substituents selected from the group consisting of OH, halogen, $O_m$(-alk)$_n CO_2R^c$ and (alk)$_n$OH.

9. The compound according to claim 8 wherein the phenyl group is substituted at the 2 and 4 positions.

10. The compound according to claim 9 wherein both substituents are halogen.

11. The compound according to claim 10 wherein the 2-substituent is fluoro and the 4-substituent is chloro.

12. The compound according to claim 1 wherein $R^1$ represents a phenyl group substituted by a 5-tetrazolyl group optionally substituted by $C_{1-3}$ alkyl.

13. The compound according to claim 1 wherein $R^1$ represents a fused group:

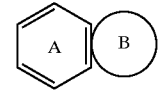

wherein B represents a furan ring optionally substituted by $CO_2(C_{1-3})$ alkyl.

14. The compound according to claim 13 wherein the furan ring is substituted in the 2 position.

15. A method of preparing a compound according to claim 1 which comprises reacting a compound of formula (II):

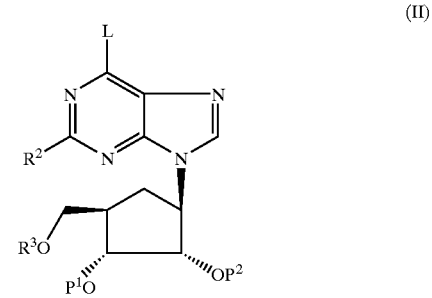

(II)

wherein $R^1$, $R^2$ and $R^3$ are as defined in claim 30, L represents a leaving group and $p^1$ and $p^2$ represent protecting groups or H; with a compound $R^1NH_2$ or a salt thereof under basic conditions.

16. A pharmaceutical composition comprising a compound according to claim 1 together with a pharmaceutically acceptable carrier and/or excipient.

17. A method of treating a patient suffering pain or epilepsy, comprising administering a therapeutically effective amount of a compound according to claim 1 to the patient.

* * * * *